(12) United States Patent
Mukasa et al.

(10) Patent No.: US 7,344,375 B2
(45) Date of Patent: Mar. 18, 2008

(54) PUSHING DEVICE FOR TOOTH RESTORATION MATERIAL MIXED AND KNEADED IN CAPSULE

(75) Inventors: Yoshihisa Mukasa, Itabashi-ku (JP); Michio Kato, Inashiki-gun (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 11/608,497

(22) Filed: Dec. 8, 2006

(65) Prior Publication Data

US 2007/0134620 A1 Jun. 14, 2007

(30) Foreign Application Priority Data

Dec. 8, 2005 (JP) .............................. 2005-354759

(51) Int. Cl.
*A61C 5/04* (2006.01)
*G01F 11/00* (2006.01)
(52) U.S. Cl. ........................................ 433/90; 222/391
(58) Field of Classification Search ............ 433/89–90; 222/386
See application file for complete search history.

(56) References Cited

U.S. PATENT DOCUMENTS 5,755,362 A * 5/1998 Rodriguez et al. ............ 433/90
6,929,157 B2 * 8/2005 Orecchia et al. ............ 222/391

* cited by examiner

*Primary Examiner*—Ehud Gartenberg
*Assistant Examiner*—Heidi M Bashaw
(74) *Attorney, Agent, or Firm*—Oblon, Spivak, McClelland, Maier & Neustadt, P.C.

(57) ABSTRACT

To improve operativity, a pushing device for a tooth restoration material mixed and kneaded in a capsule comprises a compression coil spring 4 provided between a leak preventive cover 2 contacted with a capsule and having a cylindrical piston rod 1 inserted, and a ratchet body 3 having a rack part 3*cb* and fixed to the piston rod 1; a housing body 5 having a supporting path 5*b* inserted in the leak preventive cover 2 and a guiding path 5*c* provided with the ratchet body 3 movably; a ratchet body locking plate spring 6 for preventing move of the ratchet body 3; a lever 7 for moving the rack part 3*cb* and returning the lever body 7*a* to an initial position; a release body 8 for canceling the locking to the rack part 3*cb*; and a stopper means 9 for stopping the ratchet body 3 at the initial position.

7 Claims, 4 Drawing Sheets

PUSHING DEVICE FOR TOOTH RESTORATION MATERIAL MIXED AND KNEADED IN CAPSULE

BACKGROUND OF THE INVENTION

1. Field of the Invention

The present invention relates to a pushing device for a tooth restoration material mixed and kneaded in a capsule, which are for pushing out a desired amount of the mixed and kneaded tooth restoration material toward a treating portion of a patient. A capsule for a tooth restoration material is mounted on the pushing device, and the tooth restoration material is made by mixing and kneading predetermined amounts of a powder component and a liquid component, which are isolatedly housed in the capsule so as to constitute the tooth restoration material such as dental cement or the like.

2. Description of the Conventional Art

As a dental treatment method widely used for filling the tooth restoration material such as dental cement or the like to a caries portion of a tooth, there is a treatment method comprising the steps of isolatedly housing predetermined amounts of a powder component and a liquid component constituting the tooth restoration material in one capsule for the tooth restoration material; destroying a partition wall for isolating the powder component and the liquid component in the capsule for a tooth restoration material immediately before using the tooth restoration material; mounting the capsule for a tooth restoration material on an automatic kneading device so as to mix and knead the powder component and the liquid component immediately after destroying the partition wall; setting the capsule for a tooth restoration material to a pushing device for the tooth restoration material; and pushing out a desired amount of the mixed and kneaded tooth restoration material from a nozzle of the capsule for a tooth restoration material toward a treating portion of a patient.

As for the capsule for a tooth restoration material used for such the treatment method, for example, there is a capsule for mixing and kneading a tooth restoration material therein, where the tooth restoration material consists of fixed amounts of two components, that is, a powder component and a liquid component measured in advance, and directly administering the mixture to a portion of a tooth of patient to be restored, comprising a cylinder-shaped capsule body having a mixing compartment for housing the powder component and provided with a first opening forming part on a center axis at an end thereof for forming a mixture outlet hole; a liquid cup having a liquid component housing room therein for housing the liquid component and provided with a second opening forming part on a center axis at an end thereof for forming an outlet hole for the liquid component, where the liquid cup is fitted over the cylinder-shaped portion for forming the mixing compartment of the capsule body and provided with a projection stopper on an outer surface thereof near a rear end thereof; a plunger having a rod-shaped projection for tearing the second opening forming part of the liquid cup and the first opening forming part of the capsule body and being fitted over the cylinder-shaped portion in the liquid cup; and a nozzle having an rear end, which has a shape corresponding to the front end of the capsule body and being connected to the front end of the capsule body. The projection stopper has such a size as prevent to easily take the liquid cup into the capsule body when tearing the second opening forming part so as to form the outlet hole for the liquid component, but does not prevent to take the liquid cup into the capsule body when applying large force. (for example, refer to Japanese Patent Application Laid Open No. 2002-191622.)

In order to push out the tooth restoration material toward a treating portion of a patient using such the capsule for a tooth restoration material, there is a method comprising the steps of pressing the plunger so as to tear the second opening forming part in the liquid cup and to flow the liquid component in the liquid cup into the mixing compartment of the capsule body; mixing and kneading the powder component housed in the mixing compartment in advance and the liquid component flowing-in from the liquid housing room using a kneading device for the capsule for a tooth restoration material; setting the capsule on the pushing device of the tooth restoration material; pressing the plunger so as to tear the first opening forming part of the capsule body; and pushing out a desired amount of the mixed and kneaded tooth restoration material from the nozzle of the capsule for a tooth restoration material toward a treating portion of a patient.

As the kneading device for the capsule for a tooth restoration material, which is used for mixing and kneading the powder component and the liquid component in the mixing compartment of the capsule for a tooth restoration material, for example, there is a device for mixing and kneading these components by shaking or rotating a capsule holding part for holding the capsule for a tooth restoration material.

Further, as the pushing device for the tooth restoration material, there is a device for pushing out a desired amount of the mixed and kneaded tooth restoration material from the nozzle of the capsule for a tooth restoration material toward a treating portion of a patient by using the capsule for a tooth restoration material, where the powder component and the liquid component are mixed and kneaded in the mixing compartment, comprising:

a housing body in which a mounting part of the capsule for a tooth restoration material, a guiding path, a supporting part and a reset pusher guiding path are provided at an upper part of the housing body, where the mounting part is provided at a front end, the guiding path is movably inserted with a piston rod and provided through at a front part, the supporting part supports a push plate, works as a guiding path of the piston rod and is suspended at a center part, and the reset pusher guiding path is inserted with a reset pusher mounted on a rear end of the piston rod and provided through at a rear part, a screw for adjusting a position of a stopper plate is screwed to a female screw provided just beneath the reset pusher guiding path, and a spot faced part for specifying an initial position of a lever is provided at a lower part of the front part;

a reset pusher which is inserted into the reset pusher guiding path of the housing body, has a cylindrical shape with a closed rear end and has a flange on an outer periphery of a front part thereof;

a piston rod penetrating in the guiding path of the housing body and the guiding path of the supporting part, being inserted in the reset pusher at the rear end thereof, having a fixed pitch groove at a part which is engaged with at least the push plate in the housing body, having a groove for fitting a snap ring provided at a part positioned at a rear end of the guiding path in the housing body in an initial state, having a stepped part provided at the frontward side from the groove for fitting, and having such a diameter as engages to a rear end of the capsule for a tooth restoration material at a part at frontward side from the stepped part;

a stopper plate having an upper end and a lower end constantly pressed by a spring for the stopper plate, so that the upper end contacts to an upper part of the front end of the reset pusher, and the lower end contacts to the front end of the screw for adjusting a position of the stopper plate, and having an engaging hole, where an upper end and lower end of the engaging hole are engaged with an outer periphery of the piston rod penetrating the engaging hole so as to prevent to move the piston rod in the axial direction by friction force when the stopper plate is inclined, and the upper end and the lower end of the engaging hole are not engaged with the outer periphery of the piston rod so as not to prevent to move the piston rod in the axial direction when the stopper plate becomes perpendicular to the axial center of the piston rod by frontwardly pushing of the reset pusher;

a push plate in which, when a lever is not operated, the push plate is constantly pressed by the spring for a push plate so that an rear face of an upper part contacts with a front face of the supporting part in the housing body, the push plate becomes perpendicular to the axial center of the piston rod and the engaging hole penetrated with the piston rod is not engaged with the outer periphery of the piston rod, and when the lever is operated and a top end thereof contacts with the front face of the supporting part inclined so as to be, the upper end and the lower end of the engaging hole are engaged with the outer periphery of the piston rod so as to enable to frontwardly move the piston rod by frictional force in the axial direction;

a spring for pushing back a piston rod being provided between rear face of a fixing nut and front face of a ring and giving a force for not pushing back the piston rod in the axial direction to overcome the frictional force occurred when the engaging hole of the stopper plate is engaged with the outer periphery of the piston rod, where the fixing nut is screwed at the backward side from the mounting part of the front end of the housing body, a through hole is provided in an inner surface of the fixing nut, the front part of the piston rod can be slid and moved in the axial direction in the through hole, and rear face of the ring is supported by the snap ring loosely fitted to the piston rod and engaged with the groove for fitting a snap ring of the piston rod; and a lever being rotatably mounted on a lever shaft fixed at the housing body, having a spring supporting part at a rear end of upper part thereof on which a front end of a tension spring is mounted, where a rear end of the tension spring is mounted on a spring supporting member at a rear part of the housing body, having a projection part at a front part thereof, where the projection part is contacted with the spot faced part of the housing body, and having a push plate pressing part at an upper part thereof, where the push plate pressing part is contacted with a lower end rear part of the push plate. (for example, refer to Japanese Patent Application Laid Open No. 1997-253085)

According to the above-described pushing device for a tooth restoration material mixed and kneaded in the capsule, a desired amount of the tooth restoration material can be pushed out without large force for pushing out the material from the inside of the capsule for a tooth restoration material. However, when the tooth restoration material mixed and kneaded in the capsule for a tooth restoration material is pushed out from the inside of the capsule using the pushing device for a tooth restoration material, a residual powder component or the like being not mixed and kneaded in the capsule body of the capsule for a tooth restoration material is jetted outwardly from the space between the inner periphery of the capsule body and the outer periphery of the liquid cup at the rear end part of the capsule for a tooth restoration material (especially, a powder component, which enters into a slight space existing between an inner periphery of the capsule body and an outer periphery of the liquid cup by increasing of pressure in the mixing compartment, when the plunger is pressed so as to tear the second opening forming part of the liquid cup by a rod-like projection at a top end part thereof and to flow the liquid component in the liquid cup into the mixing compartment of the capsule body). So, there are problems that the jetted powder component are poured on a face of a patient or a dentist, and a patient or a dentist inhales the powder component by mistake. Further, since the powder component enters into the housing body, there is a problem that the pushing device itself for the restoration material mixed and kneaded in the capsule causes the malfunction.

Further, the pushing device for a tooth restoration material mixed and kneaded in a capsule has the structure that, when the lever is operated so as to incline the push plate, the upper end and the lower end of the engaging hole of the push plate are engaged with the outer periphery of the piston rod in which the groove having a fixed pitch is formed at least at the part engaged with the push plate, and the piston rod is moved forward in the axial direction by the frictional force thereof. Thus, when the engaging hole of the push plate is a round hole, the engaging hole and the outer periphery of the piston rod are engaged by point contact, and when the engaging hole of the push plate is an elliptical hole, the engaging hole and the outer periphery of the piston rod are engaged by line contact with short engaging length, so that the contacting area of the engaging hole and the outer periphery of the piston rod are remarkably small. So, the force generated by operating the lever concentrates on the remarkably slight contacting area, and when the operation for moving the piston rod forward in the axial direction are repeated, the engaging hole of the push plate and the outer periphery of the piston rod are easily abraded, deformed or damaged in a short period of time, so that there is a problem that life of the push plate or the piston rod is short. Further, as described above, the residual powder component or the like being not mixed and kneaded in the capsule body of the capsule for a tooth restoration material is jetted outwardly from the rear end part of the capsule for a tooth restoration material. So, if the powder component or the like enters into the housing body so as to adhere at the outer periphery of the piston rod or the engaging hole of the push plate, the engaging hole of the push plate and the outer periphery of the piston rod are not engaged and are slid by the adhered powder component or the like at the time of operating the lever. Thus, there are problems that the piston rod cannot be moved forward in the axial direction, and an operator may be injured unexpectedly since the lever is rotated rapidly.

SUMMARY OF THE INVENTION

The present invention solves the above-described problems, and an objective of the present invention is to provide a pushing device for a tooth restoration material mixed and kneaded in a capsule, where the device is for pushing a desired amount of the tooth restoration material housed in the capsule for the tooth restoration material toward a treating portion of a patient. More particularly, it is aimed to provide a pushing device for a tooth restoration material mixed and kneaded in a capsule having excellent durability and operativity, where even if a residual powder component or the like being not mixed and kneaded in a capsule body of the capsule for a tooth restoration material is jetted outwardly from a rear end part of the capsule for a tooth restoration material, the powder component or the like are not scattered toward a patient or a dentist.

The earnest work was carried out in order to solve the above-described problems and, as a result of this, it was found out to complete the present invention that the following device is useful for solving these problems. In the device, a leak preventive cover is provided at a rear part of a mounting part, at which a capsule for a tooth restoration material is provided, of a housing body for preventing outward scatter of a powder component or the like jetted from a rear end part of the capsule for a tooth restoration material, and for inducing the powder component or the like into the housing body. Further, a mechanism for positioning and frontwardly moving the leak preventive cover is provided. The leak preventive cover is positioned to be inserted into the housing body at an initial position so as to prevent interference at the time of mounting the capsule for a tooth restoration material on the mounting part of the housing body. When the lever is operated so as to move the piston rod frontwardly, the leak preventive cover is frontwardly moved so as to be contacted with a rear end part of the capsule body for a tooth restoration material mounted on the mounting part of the housing body. Further, as a mechanism for operating the lever so as to move the piston rod frontwardly, a ratchet mechanism having durability and being operated certainly is employed. Thereby, even if the residual powder component or the like being not mixed and kneaded in the capsule body of the capsule for a tooth restoration material is jetted outwardly from the rear end part of the capsule for a tooth restoration material, the powder component or the like is not scattered toward a patient and a dentist, and further, durability and operativity can be remarkably improved.

The present invention is a pushing device for a tooth restoration material mixed and kneaded in a capsule, and the device comprising:

a cylindrical piston rod for pushing a tooth restoration material housed in a capsule for a tooth restoration material, the piston rod having a head part and a through hole, where the head part has at least a part, which has a larger outer diameter than that of the backward side, at the front end side, and the through hole is provided along the whole length of the piston rod, and having at least more than one slit at a front end thereof and locking through holes provided in a side part at the rear end side thereof, where the locking through holes have a smaller diameter than that of the through hole, reach to the through hole, and are opposed each other;

a leak preventive cover having a front end opening part contacted with a rear end part of the capsule for a tooth restoration material to be mounted, a housing part for housing the head part of the piston rod, an inserting hole for inserting a portion at the backward side from the head part of the piston rod slidably in the axial direction at the backward side of the housing part, and a small diameter portion and a large diameter portion on the outer periphery thereof, where the small diameter portion is provided at the front end side, and the large diameter portion is provided at the rear end side;

a ratchet body having an upward wall part having a release body inserting part from the frontward side to the backward side at a center part in the width direction; a frontward wall part having a piston rod inserting hole provided for inserting the rear end part of the piston rod, and both side wall parts having a hole for a piston rod fixing pin provided through at the frontward side, and having a rack part for a ratchet formed on a lower edge at the rear side of the hole for a piston rod fixing pin, wherein the piston rod inserted into the piston rod inserting hole is fixed by a piston rod fixing pin, which is inserted into the both locking through holes of the piston rod, and the both holes for a piston rod fixing pin;

a compression coil spring provided between a rear face of the leak preventive cover and a front face of the frontward wall part of the ratchet body, and along the outer periphery of the piston rod;

a housing body having a mounting part at which the capsule for a tooth restoration material is mounted, a supporting path for slidably inserting the small diameter portion of the leak preventive cover; a guiding path in which the piston rod, the compression coil spring and the ratchet body are provided movably in the front and rear directions while contacting to the upward wall part of the ratchet body, a through hole for a lever shaft provided at the both side wall parts at a lower side of the guiding path; a grip part provided at the rear end side of the guiding path; and an opening part for a release body at a position of an upper side of the guiding path, where the position is at least connected to the release body inserting part of the ratchet body when the ratchet body is moved at the most backward side so as to be positioned at an initial position and where the mounting part, the supporting path and the guiding path are provided in this order from a front end toward the back at an upper part of the housing body;

a ratchet body locking plate spring, which is for constantly giving force for upwardly pressing the ratchet body so as to prevent move of the ratchet body in the front and rear directions, and rear end of the ratchet body locking plate spring is fixed at the backward side from the guiding path in the housing body, and a locking pawl is which is at the front of the ratchet body locking plate spring is inserted into a root part of a cogs of the rack part for a ratchet of the ratchet body;

a lever having a lever body rotatably mounted on a lever shaft fixed at the through hole for a lever shaft of the housing body, a torsion spring being provided along the outer periphery of the lever shaft and constantly giving force for downwardly rotating the backward side from the lever shaft of the lever body, and a pressing body having one end part axially supported at the backward side from the lever shaft of the lever body and constantly receiving a force for inserting a pressing pawl formed at another end thereof into the root part of the cogs of the rack part for a ratchet of the ratchet body, which is positioned at the frontward side from the locking pawl of the ratchet body locking plate spring; where the force is given by a spring for a pressing body provided between the pressing body and the lever body; and where, when a portion at the backward side from the lever shaft of the lever body is upwardly rotated while resisting against the rotating force given by the torsion spring and the pressing force given by the compression coil spring and the ratchet body locking plate spring, the pressing pawl of the pressing body frontwardly presses the root part of the cogs of the rack part for a ratchet of the ratchet body so as to frontwardly move the cogs of the rack part for a ratchet body by just one cog, and when the force for upwardly rotating the portion at the backward side from the lever shaft of the lever body is canceled, the pressing pawl of the pressing body is inserted into a root part of the cogs, which is just one cog behind the cogs of the rack part for a ratchet moved by the pressing pawl of the pressing body, so as to return the lever body to the initial position;

a release body having a pressing part provided between the both side wall parts of the ratchet body, and a button part, which is continuously formed above the pressing part, has a smaller area of a transverse section than an area of a transverse section rectangular to the moving direction of the pressing part, and is projected from the opening part for a release body of the housing body, where, when the button part is downwardly pressed, the pressing part downwardly moves the locking pawl of the ratchet body locking plate spring and the pressing pawl of the pressing body of the lever, which are inserted into the root part of the cogs of the rack part for a ratchet of the ratchet body, so as to cancel the locking state to the rack part for a ratchet; and a stopper means for controlling to stop the ratchet body, which is backwardly moved by the pressing force the compression coil spring, at the initial position, when the locking state of the locking pawl of the ratchet body locking plate spring and the pressing pawl of the pressing body of the lever to the rack part for a ratchet is canceled by the release body.

Further, it was found out that the following constitutions were preferable to remarkably improve an operatability of returning the piston rod and the leak preventive cover to the backward initial position when downwardly pressing the button part of the release body. In the pushing device for a tooth restoration material mixed and kneaded in the capsule according to the present invention, an auxiliary compression coil spring is provided along the outer peripheries of the leak preventive cover and the compression coil spring, between a front end side of the guiding path of the housing body and the frontward wall part of the ratchet body. Further, a compression coil spring for a leak preventive cover having a smaller spring constant than that of the compression coil spring is provided along the outer periphery of the leak preventive cover, between a flange part formed on a rear end outer periphery of the leak preventive cover and the front end of the guiding path of the housing body.

Further, the followings were also found out. When a housing part of the leak preventive cover has a shape having a diameter which is made gradually larger toward the front end thereof, the powder component or the like jetted from the rear end part of the capsule for a tooth restoration material easily flows into the through hole of the piston rod, so that it is preferable. Further, as the spring for a pressing body of the pressing body of the lever, a compression coil spring and a plate spring, which are provided between the pressing body and the lever body, can be used. Thus, a spring for a pressing body can be suitably selected according to shapes of the housing body, the lever and the like, so that it is preferable. Further, when the stopper means controls to stop the ratchet body at the initial position by contacting a front end of the release body inserting part of the upward wall part of the backwardly moved ratchet body to the button part of the release body, and/or by contacting a rear end of the piston rod fixed at the backwardly moved ratchet body to the pressing part of he release body, the ratchet body backwardly moved by the pressing force of the compression coil spring can be controlled so as to be certainly stopped at the initial position, so that it is preferable.

Further, the following was also found out. When a smooth sliding member made of a synthetic resin and contacted with an inner face of the guiding path of the housing body is adhered on an upper face of the upward wall part and/or side faces of the both side wall parts of the ratchet body, frictional force between the ratchet body and the guiding path of the housing body can be reduced, at the time that the ratchet body is moved in front and rear directions, so that it is preferable.

The pushing device for a tooth restoration material mixed and kneaded in a capsule according to the present invention has the above-described constitution. So, the leak preventive cover is positioned in the supporting path of the housing body and the head part of the piston rod is housed in the housing part of the leak preventive cover at the initial position. Therefore, when the capsule for a tooth restoration material is mounted on the mounting part of the housing body, the leak preventive cover and the piston rod do not interfere, so that the capsule for a tooth restoration material can be easily mounted. Further, when the lever is operated so as to frontwardly move the piston rod, the leak preventive cover is frontwardly moved by the pressing force of the compression coil spring according to frontwardly moving of piston rod, and reaches to a position contacting with the rear end part of the capsule for a tooth restoration material. So, the leak preventive cover can be contacted with the rear end part of the capsule for a tooth restoration material by only an ordinary operation of the lever for pushing out the tooth restoration material housed in the capsule for a tooth restoration material. Therefore, a complicated operation is not added by the existence of the leak preventive cover, and operativity is remarkably excellent.

Further, in the case that the capsule for a tooth restoration material mounted on the mounting part of the housing body is pushed by the piston rod so as to push out the tooth restoration material housed in the capsule for a tooth restoration material, the front end opening part of the leak preventive cover is already contacted with the rear end part of the capsule for a tooth restoration material So, even when the residual powder component or the like being not mixed and kneaded in the capsule body of the capsule for a tooth restoration material is jetted from the rear end part of the capsule for a tooth restoration material, the jetted powder component or the like is not outwardly jetted due to the existence of the leak preventive cover, but flow into the housing body through the through hole of the piston rod from the slit of the piston rod and the opening of the through hole. Therefore, it can be prevented that the powder component or the like is poured on a face of a patient or a dentist, and a patient or a dentist inhale it by mistake.

Further, the present invention has the constitution that the pressing pawl has one end part axially supported to the lever body of the lever at the backward side from the lever shaft of the lever body, and is formed at another end of the pressing body. This pressing pawl frontwardly presses the root part of the cogs of the rack part for a ratchet formed at the lower edges of the both side wall parts of the ratchet body so as to frontwardly move the tooth of the rack part for a ratchet by only one cog, and the piston rod is thereby frontwardly moved. So, certainty of the operation and durability are remarkably improved comparing with the conventional device by the method of engaging the engaging hole of the push plate with the outer periphery of the piston rod so as to frontwardly move the piston rod by the frictional force. Further, all the powder component or the like jetted from the rear end part of the capsule for a tooth restoration material flow into the hosing body due to the leak preventive cover as described above. At this time, even if the powder component or the like is adhered on the outer periphery of the piston rod, the outer periphery of the leak preventive cover, the rack part for ratchet, the pressing pawl and the like, the pressing pawl certainly gets the root of the cogs of the rack part for a ratchet and frontwardly presses it. Therefore, it can be prevented to cause troubles that frontwardly moving of the piston rod is prevented and the lever is rapidly rotated.

Furthermore, the present invention has the constitution that, when the piston rod is returned to the backward initial position after pushing out the tooth restoration material housed in the capsule for a tooth restoration material, the button part of the release body is downwardly pressed, and accordingly, the locking pawl of the ratchet body locking plate spring and the pressing pawl of the pressing body of the lever, which are inserted into the root of the tooth of the rack part for a ratchet of the ratchet body by the pressing part of the release body, are downwardly moved, and the ratchet body is backwardly moved by the pressing force of the compression coil spring until being stopped by the stopper means. Thereby, the piston rod fixed at the ratchet body is returned to the initial position. This piston rod has the head part having at least the portion, which has the larger outer diameter than that of the backward side, at the front end side. The leak preventive cover, in which the piston rod is inserted, has the housing part for housing the head part of the piston rod, and has the inserting hole formed for slidably inserting the portion at the backward side from the head part of the piston rod in the axial direction, at the backward side of the housing part. So, the piston rod can be returned to the initial position by only an operation of downwardly pressing the button part of the release body. Further, the inner wall of the housing part of the leak preventive cover is backwardly pressed with the head part of the piston rod by the force caused when backwardly moving the piston rod, and thereby the leak preventive cover is moved to the initial position. Therefore, the used capsule for a tooth restoration material mounted on the housing body can be easily removed, and operativity can be remarkably improved.

Further, according to the pushing device for a tooth restoration material mixed and kneaded in a capsule according to the present invention, since if has the mechanism such as the leak preventive cover, the ratchet body and the like as described above, such the trouble that the residual powder component or the like being not mixed and kneaded in the capsule of the capsule for a tooth restoration material is jetted outwardly from the rear end part of the capsule, can be solved. Thus, it is not necessary to give processing to the capsule for a tooth restoration material itself, and the capsule for a tooth restoration material having a conventional shape can be used. So, it is economical since running cost is not increased, and a load on an earth environment is not increased. That is, if the tooth restoration material housed in a conventional capsule for a tooth restoration material remains unused after being mixed and kneaded, the material is solidified so as to be disposed with the capsule. Further, if the above-described problem can be solved by processing the capsule for a tooth restoration material or adding an adduct to the capsule, the unit cost is increased, and a material for constituting the capsule for a tooth restoration material is increased. As a result of this, it is uneconomical, and a load on an environment is increased. On the other hand, in the pushing device for a tooth restoration material mixed and kneaded in a capsule according to the present invention, the capsule for a tooth restoration material having a conventional shape can be used as it is, so that the above-described problems are not caused.

Further, in the pushing device for a tooth restoration material mixed and kneaded in a capsule according to the present invention, the auxiliary compression coil spring is provided along the outer peripheries of the leak preventive cover and the compression coil spring between the front end side of the guiding path of the housing body and the frontward wall part of the ratchet body. Further, the compression coil spring for a leak preventive cover having smaller spring constant than that of the compression coil spring is provided along the outer periphery of the leak preventive cover between the flange part formed on the rear end outer periphery of the leak preventive cover and the front end in the guiding path of the housing body. Accordingly, when the button part of the release body is downwardly pushed so as to return the piston rod and the leak preventive cover to the backward initial position, the auxiliary compression coil spring applies force to the ratchet body itself, to which the piston rod inserted into the leak preventive cover is fixed, so as to be backwardly moved based on the front end side in the guiding path of the housing body. Further, the compression coil spring for a leak preventive cover applies force to the leak preventive cover itself so as to be backwardly moved based on the front end side in the guiding path of the housing body, and this force for backwardly moving the leak preventive cover backwardly moves the ratchet body itself, to which the piston rod is fixed, based on the rear face of the leak preventive cover. Thereby, operativity for returning the piston rod and the leak preventive cover to the backward initial position can be remarkably improved, so that it is preferable. Further, even if the powder component or the like is adhered on the outer periphery of the piston rod and the outer periphery of the leak preventive cover, the piston rod and the leak preventive cover can be certainly returned to the backward initial position, so that it is preferable.

Further, the housing part of the leak preventive cover has a shape with a diameter which is made gradually larger toward the front end thereof. In such a structure, the powder component or the like jetted from the rear end part of the capsule for a tooth restoration material easily flows into the through hole of the piston rod, so that it is preferable. Further, the powder component or the like is hardly adhered on the inner face of the housing part, so that it is preferable. Furthermore, as for the spring for a pressing body of the pressing body of the lever, both of the compression coil spring and the plate spring, which are provided between the pressing body and the lever body, can be used. So, the spring for a pressing body can be suitably selected according to the shapes of the housing body, the lever and the like.

Further, the stopper means controls to stop the ratchet body at the initial position by contacting the front end of the release body inserting part of the upward wall part of the backwardly moved ratchet body to the button part of the release body, and/or by contacting the rear end of the piston rod fixed at the backwardly moved ratchet body to the pressing part of he release body. So, the ratchet body backwardly moved by the pressing force of the compression coil spring can be controlled so as to be certainly stopped at the initial position, so that it is preferable. Furthermore, the stopper means can be made by only changing the shapes of the release body inserting part of the upward wall part of the ratchet body, and the button part and the pressing part of the release body, so that it is preferable.

Further, the smooth sliding member made of a synthetic resin and contacted with the inner face of the guiding path of the housing body is adhered on the upper face of the upward wall part and/or the side faces of the both side wall parts of the ratchet body. In such a structure, the frictional force generated between the ratchet body and the guiding path of the housing body can be decreased when the ratchet body moves in the front and rear directions, so that it is preferable. Further, an operation of the whole device of the present invention can be smoothed, so that it is preferable.

DETAILED DESCRIPTION OF PREFERRED EMBODIMENT

Hereinafter, a pushing device for a tooth restoration material mixed and kneaded in a capsule according to the present invention is described concretely with drawings.

Figure 1:
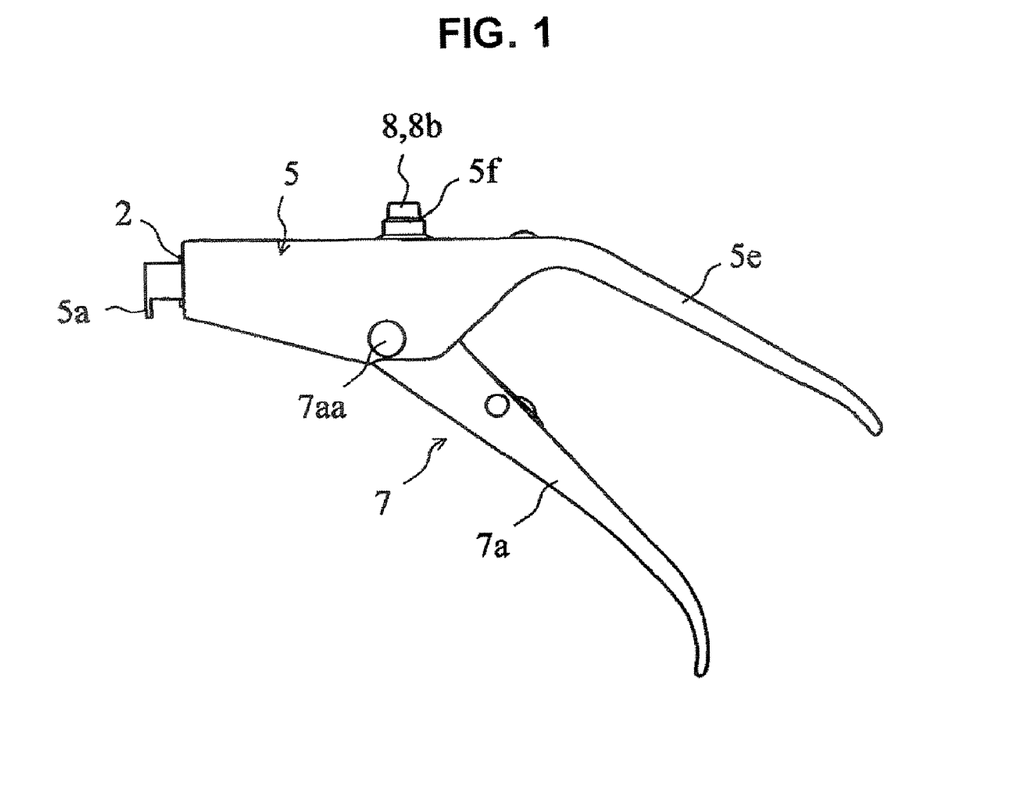
FIG. 1 is an explanatory side view illustrating an example of a pushing device 1 for a tooth restoration material mixed and kneaded in a capsule according the present invention.
Figure 2:
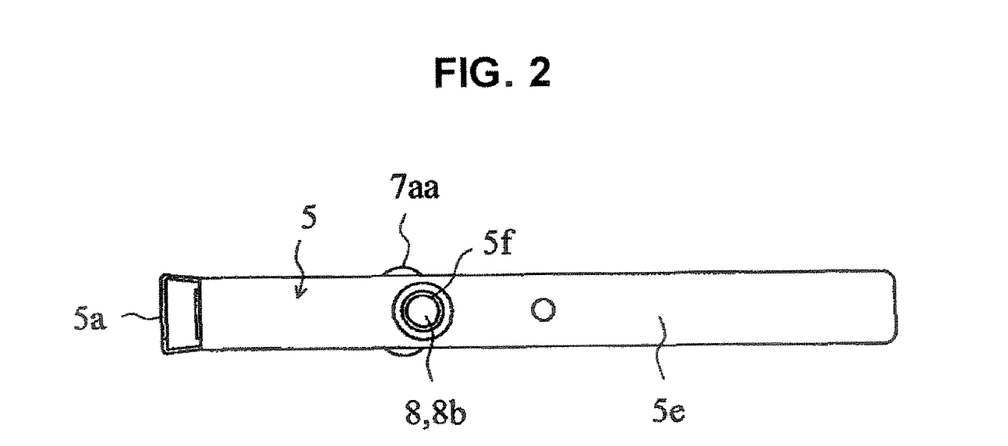
FIG. 2 is an explanatory plan view of FIG. 1.
Figure 3:
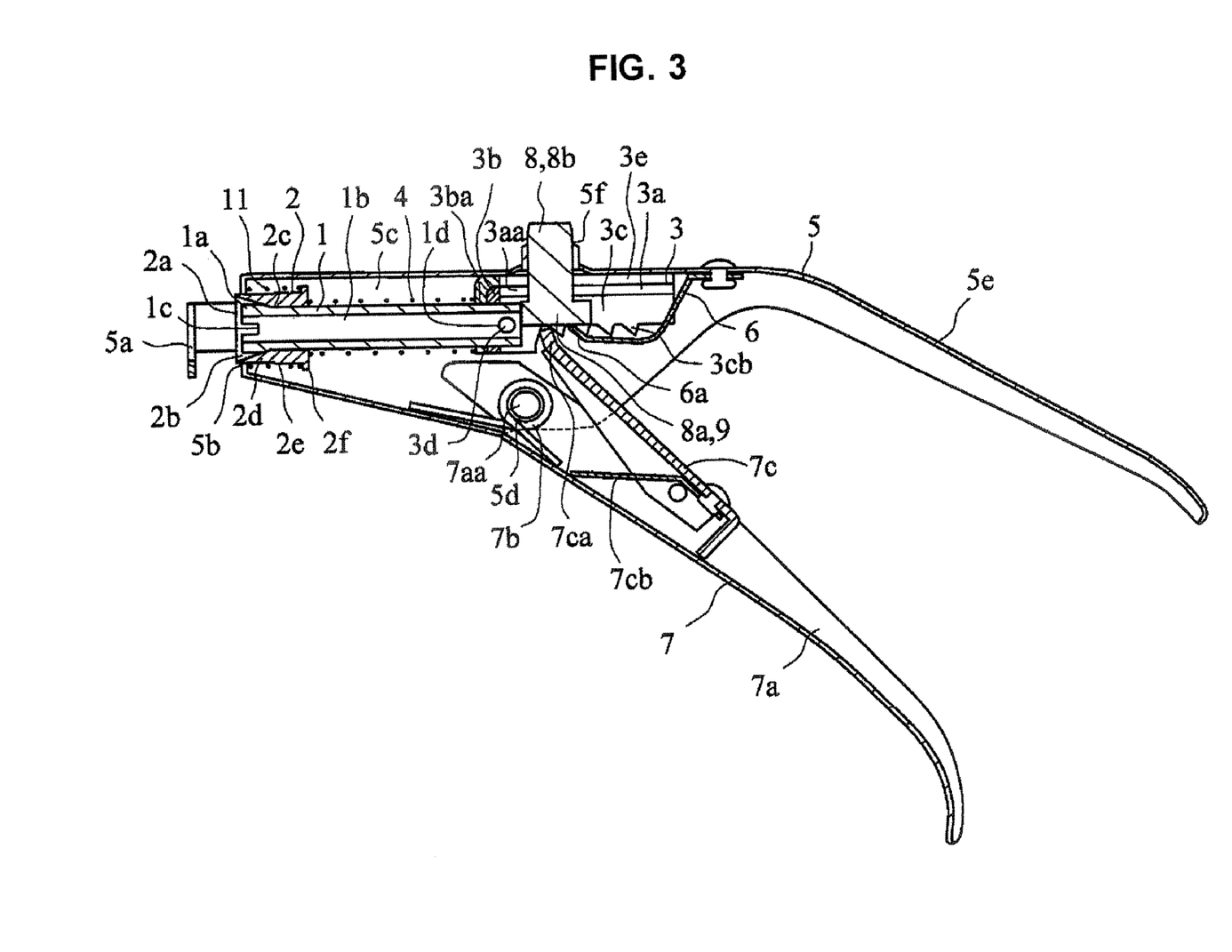
FIG. 3 is an enlarged explanatory side sectional view of FIG. 1.
Figure 4:
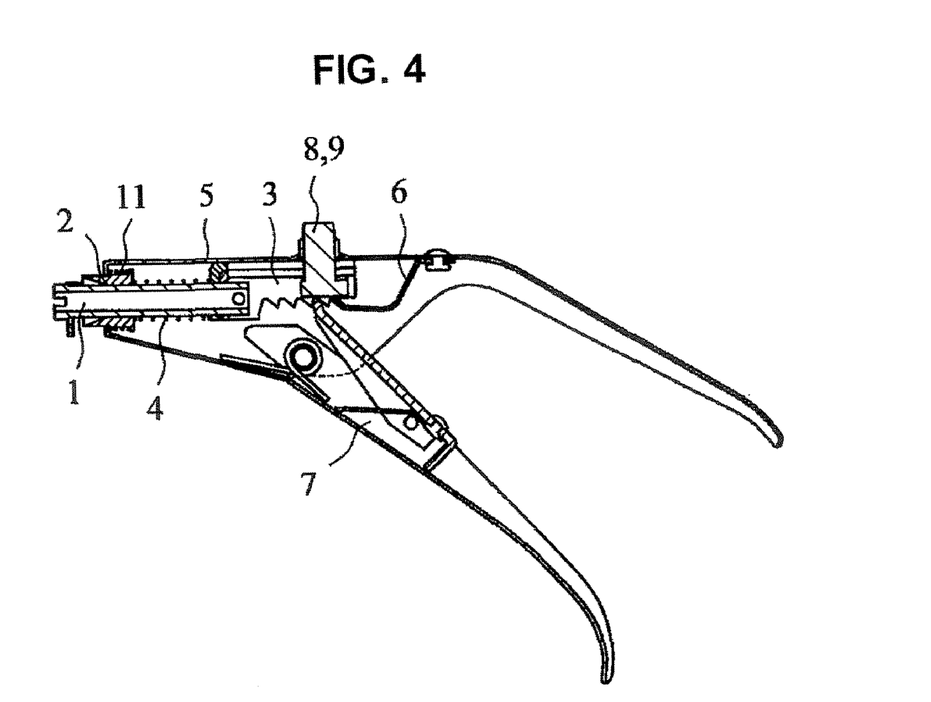
FIG. 4 is an explanatory side sectional view illustrating the state that a piston rod is frontwardly moved in the pushing device for a tooth restoration material mixed and kneaded in a capsule according to the present invention of FIG. 3.
Figure 5:
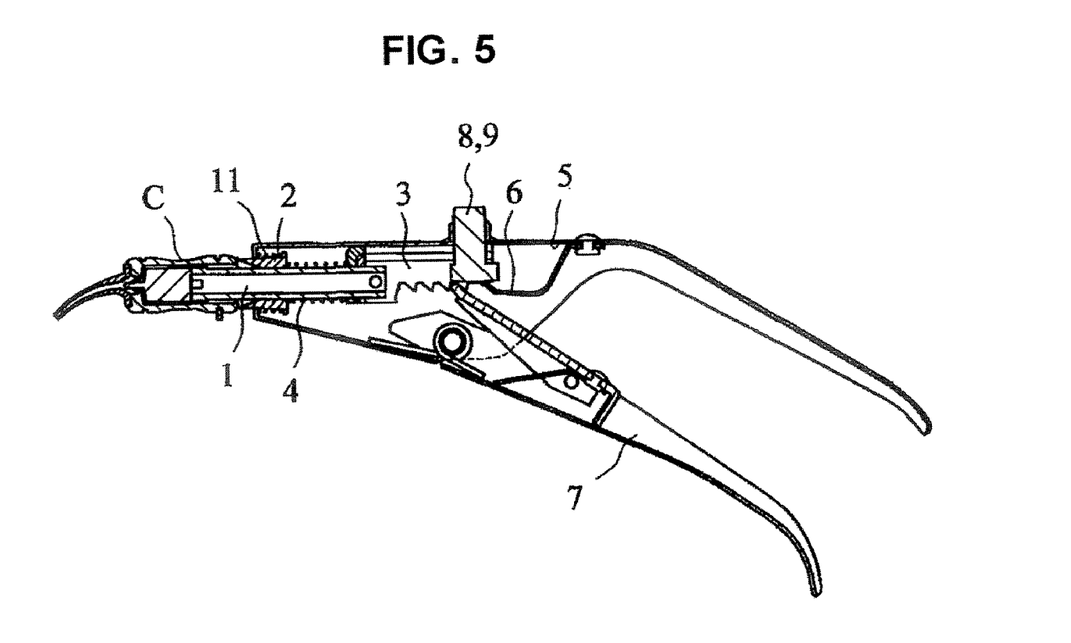
FIG. 5 is an explanatory side sectional view illustrating the state that a capsule for a tooth restoration material is mounted on the pushing device for a tooth restoration material mixed and kneaded in a capsule according to the present invention of FIG. 3, and the tooth restoration material is pushed out.
Figure 6:
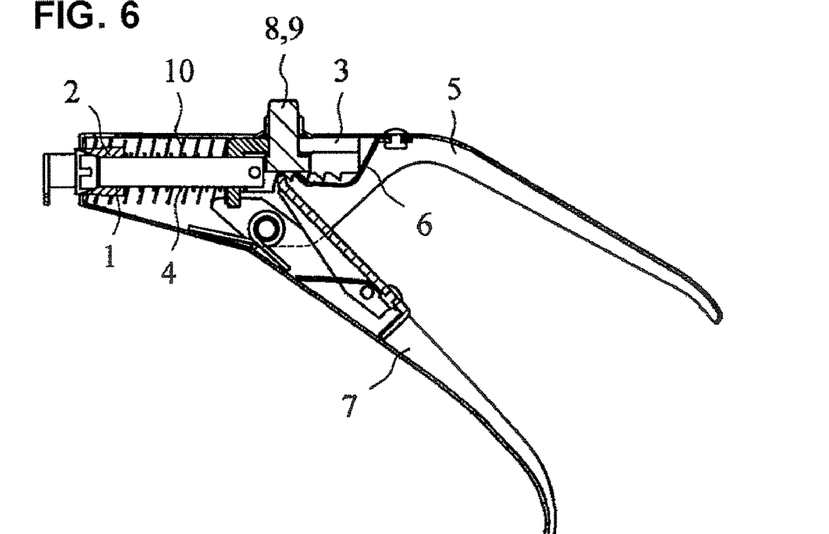
FIG. 6 is an explanatory side sectional view illustrating another example of a pushing device for a tooth restoration material mixed and kneaded in a capsule according the present invention.
Figure 7:
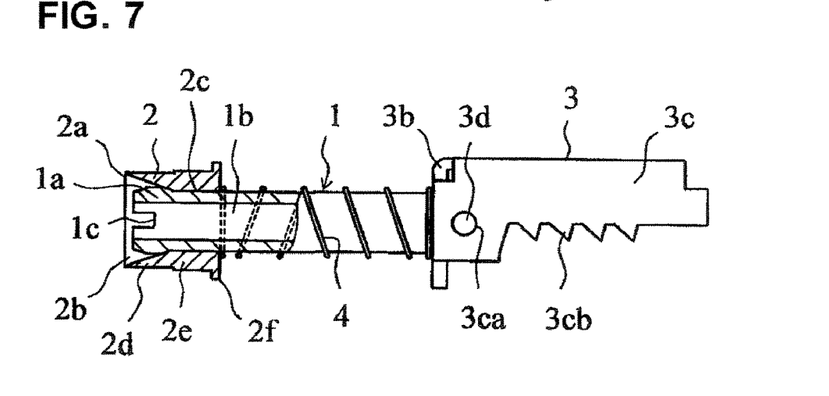
FIG. 7 is an explanatory partial side sectional view illustrating the state that a piston rod, a leak preventive cover, a ratchet body and a compression coil spring, which are used in the present invention, are assembled.
Figure 8:
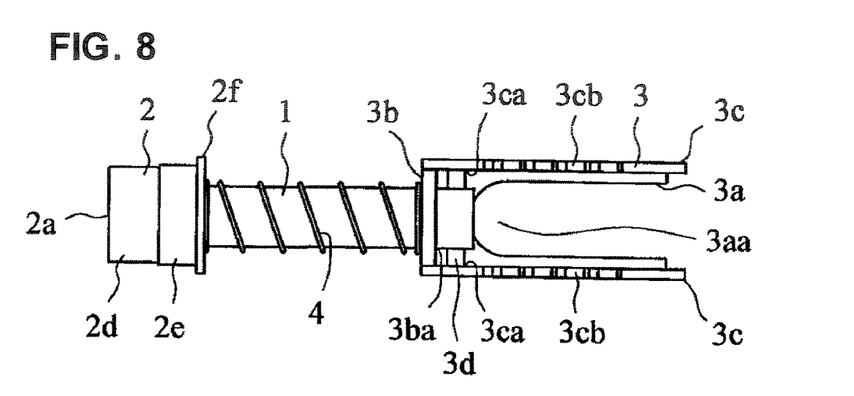
FIG. 8 is an explanatory view of a bottom face of FIG. 7.

FIG. 1 is an explanatory side view illustrating an example of a pushing device 1 for a tooth restoration material mixed and kneaded in a capsule according the present invention. FIG. 2 is an explanatory plan view of FIG. 1. FIG. 3 is an enlarged explanatory side sectional view of FIG. 1. FIG. 4 is an explanatory side sectional view illustrating the state that a piston rod is frontwardly moved in the pushing device for a tooth restoration material mixed and kneaded in a capsule according to the present invention of FIG. 3. FIG. 5 is an explanatory side sectional view illustrating the state that a capsule for a tooth restoration material is mounted on the pushing device for a tooth restoration material mixed and kneaded in a capsule according to the present invention of FIG. 3, and the tooth restoration material is pushed out. FIG. 6 is an explanatory side sectional view illustrating another example of a pushing device for a tooth restoration material mixed and kneaded in a capsule according the present invention. FIG. 7 is an explanatory partial side sectional view illustrating the state that a piston rod, a leak preventive cover, a ratchet body and a compression coil spring, which are used in the present invention, are assembled. FIG. 8 is an explanatory view of a bottom face of FIG. 7.

In the drawings, a cylindrical piston rod 1 is for pushing out a tooth restoration material housed in a capsule C for a tooth restoration material, and the piston rod 1 has a head part 1a, which at least has a part having a larger outer diameter than that of the backward side at the front end side thereof; a through hole 1b along the whole length of the piston rod (1); at least more than one slit 1c at a front end thereof; and locking through holes 1d, 1d provided in a side part at the rear end side thereof, where the locking through holes 1d, 1d have a smaller diameter than that of the through hole 1b, reach to the through hole 1b, and are opposed each other. The piston rod 1 is inserted into a leak preventive cover 2 from the rear end side thereof, and is fixed to a ratchet body 3 in the state that a compression coil spring 4 is provided along an outer periphery of the piston rod 1. A front end of the piston rod 1 presses the capsule C for a tooth restoration material mounted on a housing body 5 so as to push out the mixed and kneaded tooth restoration material housed in the capsule C for a tooth restoration material. Further, the piston rod 1 guides powder component or the like, which is jetted from a rear end part of the capsule C for a tooth restoration material, into the housing body 5.

The piston rod 1 has the head part 1a, which at least has the part having a larger diameter than that of the backward side, at the front end side thereof, as illustrated in FIGS. 3 to 7. At an initial position, the head part 1a of the piston rod 1 is housed in a housing part 2b of a leak preventive cover 2, as illustrated in FIGS. 3 and 6. When a ratchet body 3, to which the piston rod 1 is fixed, is frontwardly moved, the head part 1a is frontwardly moved so as to press the capsule C for a tooth restoration material, as illustrated in FIG. 5. When the ratchet body 3 is returned to the backward initial position by pressing of are lease body 8, the head part 1a is re-housed in the housing part 2b, and backwardly presses an inner wall of the housing part 2b so as to move the leak preventive cover 2 to the initial position.

Further, the piston rod 1 has the through hole 1b along the whole length thereof, and has at least more than one slit 1c at the front end thereof, as illustrated in FIGS. 3 to 7. When the front end of the piston rod 1 presses the capsule C for a tooth restoration material, the powder component or the like jetted from the rear end part of the capsule C for a tooth restoration material enters into the through hole 1b from the slit 1c and an opening of the through hole 1b, and reach into the housing body 5.

Further, the piston rod 1 has the locking through holes 1d, 1d in the side part at the rear end side thereof, where the holes 1d, 1d have a smaller diameter than that of the through hole 1b, reach to the through hole 1b and are opposed each other, as illustrated in FIGS. 3 to 5. The locking through holes 1d, 1d are for fixing the piston rod 1 to the ratchet body 3, where the piston rod 1 is fixed by inserting a piston rod fixing pin 3d of the ratchet body 3 from one of holes 3ca for a piston rod fixing pin of the ratchet body 3, penetrating the holes 1d, 1d, and reaching to the other of holes 3ca for a piston rod fixing pin.

A leak preventive cover 2 has a front end opening part 2a contacted with the rear end part of the capsule C for a tooth restoration material to be mounted; a housing part 2b for housing the head part 1a of the piston rod 1; an inserting hole 2c for slidably inserting a part at the backward side from the head part 1a of the piston rod 1 at the backward side of the housing part 2b in the axial direction; a small diameter portion 2d provided at the front end side on the outer periphery thereof; and a large diameter portion 2e provided at the rear end side on the outer periphery thereof. Thereby, even if the residual powder component or the like being not mixed and kneaded in the capsule body of the capsule C for a tooth restoration material is jetted from the rear end part of the capsule C for a tooth restoration material, the leak preventive cover 2 prevents the jetted powder component from outwardly scattering, so that the jetted component is not poured on a face of a patient or a dentist, and a patient or a dentist does not inhale the component by mistake.

The leak preventive cover 2 has the front end opening part 2a contacted with the rear end part of the capsule C for a tooth restoration material to be mounted, and the housing part 2b for housing the head part 1a of the piston rod 1, as illustrated in FIGS. 3 to 7. The head part 1a of the piston rod 1 is housed in the housing part 2b of the leak preventive cover 2 so as not to interfere at the time of mounting the capsule C for tooth restoration material on a mounting part 5a of a housing body 5 in the state that the piston rod 1 is positioned at the initial position.

The housing part 2b of the leak preventive cover 2 can have any shapes if it can house at least the head part 1a of the piston rod 1. However, if the housing part 2b has a shape having a diameter which is gradually made larger toward the front end thereof as illustrated in FIGS. 3 to 7, the powder component or the like jetted from the rear end part of the capsule C for a tooth restoration material easily flows into the through hole 1b of the piston rod 1, so that it is preferable. Further, the powder component or the like is not adhered on the inner face of the housing part 2b, so that it is preferable.

Further, the leak preventive cover 2 has the small diameter portion 2d at the front end side and the large diameter portion 2e at the rear end side, on the outer periphery thereof, as illustrated in FIGS. 7 and 8. In the leak preventive cover 2, the small diameter portion 2d at the front end side is supported in the state of being slidably inserted into a supporting path 5b of the housing body 5, as illustrated in FIGS. 3 and 6. Further, when the leak preventive cover 2 is frontwardly moved, as illustrated in FIGS. 4 and 5, a front end of the large diameter portion 2e at the rear end side is contacted with a front end in a guiding path 5c of the housing body 5. Thereby, the whole leak preventive cover 2 is controlled so as not to be frontwardly jumped out from the supporting path 5b of the housing body 5.

Further, as illustrated in FIGS. 3 to 5, the leak preventive cover 2 has a flange part 2f on a rear end outer periphery thereof, and a compression coil spring 11 for a leak preventive cover, which has a smaller spring constant than that of a compression coil spring 4 described below. The coil spring 11 is provided along the outer periphery of the leak preventive cover 2 between the flange part 2f and the front end in the guiding path 5c of the housing body 5. Thus, the leak preventive cover 2 itself can receive backwardly moving force, based on the front end side in the guiding path 5c of the housing body 5, and this backwardly moving force for the leak preventive cover 2 can backwardly move the ratchet body 3 itself, to which the piston rod 1 is fixed, based on a rear face of the leak preventive cover 2. Therefore, operativity when returning the piston rod 1 and the leak preventive cover 2 to the backward initial position can be remarkably improved, so that it is preferable. Further, even if the powder component or the like is adhered on the outer periphery of the piston rod 1 and the outer periphery of the leak preventive cover 2, the piston rod 1 and the leak preventive cover 2 can be certainly returned to the initial position, so that it is preferable.

The reason why the spring constant of the compression coil spring 11 for a leak preventive cover is necessarily to be smaller than that of the compression coil spring 4 in this embodiment is as follows. If the spring constant of the compression coil spring 11 for a leak preventive cover is larger than the compression coil spring 4, when the ratchet body 3 is frontwardly moved, the compression coil spring 4 is compressed before the compression coil spring 11 for a leak preventive cover is compressed, so that only the piston rod 1 is frontwardly moved. In such a case, the piston rod 1 presses the capsule C for a tooth restoration material in the state that the leak preventive cover 2 is not contacted with the rear end part of the capsule C for a tooth restoration material, and as a result of this, the residual powder component or the like, which is not mixed and kneaded in the capsule body of the capsule C for a tooth restoration material, is jetted outwardly from the rear end part of the capsule C for a tooth restoration material.

A ratchet body 3 has, from the frontward side to the backward side at a center part in the width direction, an upward wall part 3a having a release body inserting part 3aa; a frontward wall part 3b having a piston rod inserting hole 3ba provided for inserting the rear end part of the piston rod 1; and both side wall parts 3c, 3c having a holes 3ca for a piston rod fixing pin which are provided through at the frontward side, and having a rack part 3cb for a ratchet formed at a lower edge at the rear side of the holes 3ca for a piston rod fixing pin. The piston rod 1 inserted into the piston rod inserting hole 3ba is fixed with the ratchet body 3 by a piston rod fixing pin 3d inserted into the both locking through holes 1d, 1d and the both holes 3ca, 3ca for a piston rod fixing pin. The ratchet body 3 is frontwardly moved by a pressing pawl 7ca of a pressing body 7c of a lever 7 while resisting against a compression coil spring 4, so as to frontwardly move the piston rod 1 and the leak preventive cover 2.

The ratchet body 3 includes the upward wall part 3a, the frontward wall part 3b, and the both side wall parts 3c, 3c. The upward wall part 3a has the release body inserting part 3aa from the frontward side to the backward side at the center part in the width direction. The release body inserting part 3aa is inserted with a button part 8b of a release body 8, as illustrated in FIGS. 3 to 6.

The frontward wall part 3b of the ratchet body 3 has the piston rod inserting hole 3ba provided for inserting the rear end part of the piston rod 1, and the both side wall parts 3c, 3c of the ratchet body 3 respectively have the holes 3ca for a piston rod fixing pin provided through at the frontward side thereof. When the piston rod 1 is fixed to the ratchet body 3, the piston rod 1 is inserted into the front end opening part 2a of the leak preventive cover 2 from the rear end side thereof, and a compression coil spring 4 is provided along the outer periphery of the piston rod 1 projected from the rear end side of the leak preventive cover 2. Then, the rear end of the piston rod 1 is inserted into the piston rod inserting hole 3ba of the frontward wall part 3b of the ratchet body 3, so as to arrange the locking through holes 1d, 1d and the holes 3ca for a piston rod fixing pin, 3ca of the both side wall parts 3c, 3c of the ratchet body 3 approximately in line when seeing from the side wall part 3c side. After that, the piston rod fixing pin 3d is inserted from any one of the holes 3ca, 3ca for a piston rod fixing pin into the both locking through holes 1d, 1d and the both holes 3ca, 3ca for a piston rod fixing pin. Thereby, the piston rod 1 is fixed at the ratchet body 3 as illustrated in FIGS. 7 and 8.

Further, the both side wall parts 3c, 3c of the ratchet body 3 have a rack part 3cb for a ratchet formed at a lower edge at the rear side of the holes 3ca for a piston rod fixing pin, as illustrated in FIGS. 7 and 8. The rack part 3cb for a ratchet is constantly given the force for upwardly pressing by a locking pawl 6a of a ratchet body locking plate spring 6, which is inserted into a root part of the cogs of the rack part 3cb, so as to prevent move of the ratchet body 3 itself in the front and rear directions. Further, the rack part 3cb for a ratchet is frontwardly pressed by the force larger than the force upwardly pressing by the a locking pawl 6a of the ratchet body locking plate spring 6, so as to move frontwardly the ratchet body 3 itself. The frontwardly pressing force is given by a pressing pawl 7ca of a pressing body 7c of a lever 7 which is inserted into a root part of the cogs of the ratchet body 3 and positioned at the frontward side from the root part of the cogs of the ratchet body 3, in which the locking pawl 6c of the ratchet body locking plate spring 6 is inserted.

As for the rack part 3cb for a ratchet of the both side wall parts 3c of the ratchet body 3, it is not limited especially if it has a rack shape having a plurality of the cogs capable of preventing move of the ratchet body 3 itself in front and rear directions by the ratchet body locking plate spring 6 as described above, and capable of frontwardly moving the ratchet body 3 itself by a lever 7. However, if the tooth of the rack part 3cb for a ratchet has a shape in which the length of a front side of the root part is shorter than the length of a back side as illustrated in FIGS. 3 to 8, the ratchet body 3 can be frontwardly moved smoothly, so that it is preferable.

Further, a flat part not having the cogs is formed at the backward side of the rack part 3cb for a ratchet as illustrated in FIGS. 3 to 8. When the root part of the cogs is frontwardly pressed by the pressing pawl 7ca in the state that a pressing pawl 7ca of a pressing body 7c of a lever 7 is inserted into a root part of the cogs at the most backward side of the rack part 3cb for a ratchet, that is, the state just before the tooth restoration material mixed and kneaded in the capsule body of the capsule C for a tooth restoration material is finally pushed out by the piston rod 1, a locking pawl 6a of a ratchet body locking plate spring 6 is contacted with the flat part not having the cogs formed at the backward side of the rack part 3cb for a ratchet so as not enable to prevent move of the ratchet body in the front and rear direction. So, the ratchet body 3 can be freely moved in the front and rear directions by rotating a lever body 7a of the lever 7 by small force. Thereby, by adjusting the pressing force given to the capsule C for a tooth restoration material by the piston rod 1, the amount of the tooth restoration material pushed out from the inside of the capsule C for a tooth restoration material can be freely adjusted, so that it is preferable.

The tooth restoration material mixed and kneaded in the capsule generally needs a large space for mixing and kneading, so that the amount of the material is little to a size of the capsule, and has remarkably high viscosity. So, in the case of the general capsule C for a tooth restoration material, only after the pressing part of the plunger or the like in the capsule C for a tooth restoration material is frontwardly slid to a position near the front end thereof, the tooth restoration material in the capsule C for a tooth restoration material is pushed out. Thus, in the mode that the part not having a tooth is formed at the backward side of the rack part 3cb for a ratchet as described above, the constitution is made such that the pressing part of the plunger or the like in the capsule C for a tooth restoration material is moved by the piston rod 1 to a position near the front end, that is, a position just before the tooth restoration material in the capsule C for a tooth restoration material is finally pushed out, in the state that the pressing pawl 7ca of the pressing body 7c of the lever 7 is inserted into the root part of the cogs at the most backward side of the rack part 3cb for a ratchet. Thereby, the amount of the tooth restoration material pushed out from the inside of the capsule C for a tooth restoration material can be freely controlled by operating the lever body 7a of the lever 7 described below.

Further, the upward wall part 3a and the both side wall parts 3c, 3c of the ratchet body 3 are formed with a smooth member made of a synthetic resin, although it is not illustrated in the drawings, or a smooth sliding member 3e made of a synthetic resin, which is contacted with the inner face of the guiding path 5c of the housing body 5, is adhered on the upper face of the upward wall part 3a and/or side faces of the both side wall parts 3c, 3c of the ratchet body 3 as illustrated in FIGS. 3 to 5. In such the constitution, when the ratchet body 3 is moved in the front and rear directions, frictional force generated between the ratchet body 3 and the guiding path 5c of the housing body 5 can be decreased, so that it is preferable. In addition to this, an operation of the whole device of the present invention can be smoothed, so that it is preferable. Especially, in the constitution that the smooth sliding member 3e made of a synthetic resin, which is contacted with the inner face of the guiding path 5c of the housing body 5, is adhered on the upper face of the upward wall part 3a and/or side faces of the both side wall parts 3c, 3c of the ratchet body 3, when the upward wall part 3a or the both side wall parts 3c, 3c of the ratchet body 3 are made of metal, the operation of the whole device of the present invention can be smoothed without decreasing rigidity of the ratchet body 3 itself, so that it is preferable. Further, as the synthetic resin, a material such as a silicon based material, a fluorine compound, a polyoxymethylene resin (POM) or the like can be desirably used.

A compression coil spring 4 is provided between the rear face of the leak preventive cover 2 and the front face of the frontward wall part 3b of the ratchet body 3, and is provided along the outer periphery of the piston rod 1. The compression coil spring 4 constantly give force for frontwardly pressing the leak preventive cover 2 so as to contact the front end opening part 2a of the leak preventive cover 2 to the rear end part of the capsule C for a tooth restoration material mounted on a mounting part 5a at a front end of a housing body 5 described below. Further, the compression coil spring 4 constantly gives force for backwardly pressing the ratchet body 3 so as to return the ratchet body 3 to the initial position when the locking state of a ratchet body locking plate spring 6 and a lever 7 to the ratchet body 3 is canceled by pressing a release body 8 described below.

The compression coil spring 4 is provided along the outer periphery of the piston rod 1, between the rear face of the preventive cover 2 and the front face of the frontward wall part 3b of the ratchet body 3, as illustrated in FIGS. 7 and 8. The compression coil spring 4 is for keeping the state that the head part 1a of the piston rod 1 is contacted with the housing part 2b of the leak preventive cover 2. The ratchet body 3 is frontwardly moved so as to contact the front end opening part 2a of the leak preventive cover 2 to the rear end part of the capsule C for a tooth restoration material, and/or to contact the front end of the large diameter portion 2e of the leak preventive cover 2 to the front end in the guiding path 5c of the housing body 5, and after that, the ratchet body is frontwardly moved more. Thereby, the distance between the rear face of the leak preventive cover 2 and the front face of the frontward wall part 3b of the ratchet body 3 is shortened and the compression coil spring 4 is compressed, as the head part 1a of the piston rod 1 projects to more frontward position beyond the front end opening part 2a of the leak preventive cover 2 from the state of contacting to the housing part 2b of the leak preventive cover 2. Thereby, the locking state of the ratchet body locking plate spring 6 and the lever 7 to the ratchet body 3 is canceled. At this time, the compression coil spring 4 generates pressing force for returning the ratchet body 3 to the initial position.

Further, in addition to the compression coil spring 4, an auxiliary compression coil spring 10 can be provided between the front end side of the guiding path 5c of the housing body 5 and the frontward wall part 3b of the ratchet body 3, and along the outer peripheries of the leak preventive cover 2 and the compression coil spring 4, as illustrated in FIG. 6. Further, a compression coil spring 11 for a leak preventive cover having a smaller spring constant than that of the compression coil spring 4 can be provided between the flange part 2*f*, which is formed on the rear end outer periphery of the leak preventive cover 2, and the front end of the guiding path 5*c* of the housing body 5, and along the outer periphery of the leak preventive cover 2, as illustrated in FIGS. 3 to 5. In such the constitution, when a button part 8*b* of a release body 8 is downwardly pressed so as to return the piston rod 1 and the leak preventive cover 2 to the backward initial position, the auxiliary compression coil spring 10 gives force for backwardly moving the ratchet body 3 itself, to which the piston rod 1 inserted in the leak preventive cover 2 is fixed, based on the front end side in the guiding path 5*c* of the housing body 5. Further, the compression coil spring 11 for a leak preventive cover gives force for backwardly moving the leak preventive cover 2 itself, based on the front end side in the guiding path 5*c* of the housing body 5, and gives force for backwardly moving the leak preventive cover 2 backwardly moves the ratchet body 3 itself, to which the piston rod 1 is fixed, based on the rear face of the leak preventive cover 2. Therefore, operativity when returning the piston rod 1 and the leak preventive cover 2 to the backward initial position can be remarkably increased, so that, it is preferable. Further, even if the powder component or the like is adhered on the outer peripheries of the piston rod 1 and the leak preventive cover 2, the piston rod 1 and the leak preventive cover 2 can be certainly returned to the backward initial position, so that it is preferable.

A housing body 5 has a mounting part 5*a* on which the capsule C for a tooth restoration material is mounted; a supporting path 5*b* in which the small diameter portion 2*d* of the leak preventive cover 2 is slidably inserted; a guiding path 5*c* in which the piston rod 1, the compression coil spring 4 and the ratchet body 3 are provided movably in the front and rear directions in the state of contacting to the upward wall part 3*a* of the ratchet body 3; a through hole 5*d* for a lever shaft provided at the both side wall parts below the guiding path 5*c*; a grip part 5*e* provided at the rear end side; and an opening part 5*f* for a release body at a position of an upper side of the guiding path 5*c*, where this position is at least connected with the release body inserting part 3*aa* of the ratchet body 3 when the ratchet body 3 is moved to the most backward side so as to be positioned at the initial position. In the housing body 5, the mounting part 5*a*, the supporting path 5*b* and the guiding path 5*c* are provided in this order from a front end toward the rear at an upper part thereof. The housing body 5 is mounted with the capsule C for a tooth restoration material, and is for supporting each member.

The housing body 5 has the mounting part 5*a* at the front end of the upper part thereof for mounting the capsule C for a tooth restoration material. For example, the mounting part 5*a* can have a shape so as to hold the rear end part of the capsule C for a tooth restoration material, or a shape so as to only put the rear end part of the capsule C for a tooth restoration material, although the shape is not illustrated in the drawings. Further, the mounting part 5*a* can have an engaging part projecting from the front end side of the supporting path 5*b*, so as to engage to a groove part formed on the outer periphery of the rear end part of the capsule C for a tooth restoration material, as illustrated in FIGS. 1 to 5.

At the rear side of the mounting part 5*a* at the front end of the housing body 5, as illustrated in FIGS. 3 to 6, the supporting path 5 band the guiding path 5 care provided in this order. In the supporting path 5*b*, the small diameter portion 2*d* of the leak preventive cover 2 is slidably inserted. The guiding path 5*c* has the piston rod 1, the compression coil spring 4 and the ratchet body 3 which are provided movably in the front and rear directions while contacting to the upward wall part 3*a* of the ratchet body 3. The piston rod 1, the leak preventive cover 2, the ratchet body 3 and the compression coil spring 4 are integrally assembled as illustrated in FIGS. 7 and 8. These assembled parts are provided movably in the front and rear directions in the guiding path 5*c*, as illustrated in FIGS. 3 to 6, in the state that the small diameter portion 2*d* of the leak preventive cover 2 is slidably supported by the supporting path 5*b*, and in the state that root parts of teeth of the rack parts 3*cb*, 3*cb* for a ratchet of the both sidewall parts 3*c*, 3*c* of the ratchet body 3 are upwardly pressed by a locking pawl 6*a* of a ratchet body locking plate spring 6 and a pressing pawl 7*ca* of a pressing body 7*c* of a lever 7.

The guiding path 5*c* of the housing body 5 has the through holes 5*d* for a lever shaft on the both side walls at the lower part thereof, and has the grip part 5*e* on the rear end side thereof as illustrated in FIGS. 1 to 6. The through holes 5*d* for a lever shaft are for rotatably mounting a lever body 7*a* of a lever 7 by a lever shaft 7*aa*, and the grip part 5*e* is used when operating the lever body 7*a* of the lever 7. More particularly, the lever body 7*a* of the lever 7 is operated by upwardly moving it using the inner sides of fingers while contacting the upper part of the grip part 5*e* with a palm.

Further, the housing body 5 has the opening part 5*f* for a release body at the position at the upper part of the guiding path 5*c*, where the position is at least connected with the release body inserting part 3*aa* of the ratchet body 3 when the ratchet body 3 is moved to the most backward side so as to be positioned at the initial position. The opening part 5*f* for a release body is for inserting a button part 8*b* of a release body 8, which is provided between the both side wall parts 3*c*, 3*c* of the ratchet body 3 in the guiding path 5*b* of the housing body 5, as illustrated in FIGS. 3 to 6.

A ratchet body locking plate spring 6 has a locking pawl 6*a*, is for constantly giving force for upwardly pressing the ratchet body 3 so as to prevent move of the ratchet body 3 in the front and rear directions. A rear end of the locking pawl 6*a* is fixed at the backward side from the guiding path 5*c* in the housing body 5, and a front end of the locking pawl 6*a* is inserted into a root part of the cogs of the rack part 3*cb* for a ratchet of the ratchet body 3. The plate spring 6 is for supporting the piston rod 1, the leak preventive cover 2, the ratchet body 3 and the compression coil spring 4, which are provided in the guiding path 5*c* of the housing body 5 and are integrally assembled as illustrated in FIGS. 7 and 8. Further, the plate spring 6 is for supporting a release body 8, which is provided between the both side wall parts 3*c*, 3*c* of the ratchet body 3. Furthermore, the plate spring 6 is for locking the ratchet body 3 while resisting against the pressing force by the compression coil spring 4, so that the ratchet body 3 frontwardly moved by a lever 7 can keep the position after being moved.

When the lever 7 is not operated, the locking pawl 6*a* at the front end of the ratchet body locking plate spring 6 is inserted into the root part of the cogs of the rack part 3*cb* for a ratchet of the ratchet body 3 as illustrated in FIGS. 3 and 6, and the ratchet body locking plate spring 6 constantly gives the force for upwardly pressing the ratchet body 3, so as to prevent move of the ratchet body 3 in the front and rear directions. When the lever 7 is operated so as to frontwardly move the ratchet body 3, the locking pawl 6*a* inserted into the root part of the cogs of the rack part 3*cb* for a ratchet of the ratchet body 3 is pressed gradually and downwardly by a crest part of the cogs of the rack part 3*cb* for a ratchet according to frontwardly moving of the rack part 3*cb* for a ratchet. Further, when the locking pawl 6*a* passes a top point of the cogs of the rack part 3*cb* for a ratchet by further frontwardly moving of the rack part 3*cb* for a ratchet, the locking pawl 6*a* is inserted into a root part of the cogs which is just behind the above-described cogs, so as to be again in a state of preventing move of the ratchet body 3 in the front and rear directions.

A lever 7 has a lever body 7*a* rotatably mounted on a lever shaft 7*aa* fixed at the through hole 5*d* for a lever shaft of the housing body 5; a torsion spring 7*b* being provided along the outer periphery of the lever shaft 7*aa* and constantly giving force for downwardly rotating the backward side from the lever shaft 7*aa* of the lever body 7*a*; and a pressing body 7*c* having one end part axially supported at the backward side from the lever shaft 7*aa* of the lever body 7*a*, and constantly giving force for inserting a pressing pawl 7*ca* formed at another end thereof into the root part of the cogs of the rack part 3*cb* for a ratchet of the ratchet body 3, which is positioned at the frontward side from the locking pawl 6*a* of the ratchet body locking plate spring 6. This force is given by a spring 7*cb* for a pressing body provided between the pressing body 7*c* and the lever body 7*a*. In the lever 7, when a portion at the backward side from the lever shaft 7*aa* of the lever body 7*a* is upwardly rotated, the pressing pawl 7*ca* of the pressing body 7*c* frontwardly presses the root part of the cogs of the rack part 3*cb* for a ratchet of the ratchet body 3 so as to frontwardly move the tooth of the rack part 3*cb* for a ratchet body to the just frontward position by one cog. At this time, the force for upwardly rotating is given while resisting against the rotating force given by the torsion spring 7*b* and the pressing force by the compression coil spring 4 and the ratchet body locking plate spring 6. When the force for upwardly rotating is canceled, the pressing pawl 7*ca* of the pressing body 7*c* is inserted into a root part of the cogs, which is just behind the cog of the rack part 3*cb* for a ratchet moved by the pressing pawl 7*ca* of the pressing body 7*c*, so as to return the lever body 7*a* to the initial position. The lever 7 is for frontwardly moving the leak preventive cover 2 so as to contact the front end opening part 2*a* of the leak preventive cover 2 with the rear end part of the capsule C for a tooth restoration material mounted on the mounting part 5*a* of the housing body 5, and is for frontwardly moving the piston rod 1 so as to press the rear end part of the capsule C for a tooth restoration material.

The lever body 7*a* of the lever 7 is rotatably mounted on the lever shaft 7*aa* fixed at the through hole 5*d* for a lever shaft of the housing body 5, and is constantly given the force for downwardly rotating the backward side from the lever shaft 7*aa* of the lever body 7*a* by the torsion spring 7*b* provided along the outer periphery of the lever shaft 7*aa*, as illustrated in FIGS. 1 to 6. When the lever 7 is operated so as to frontwardly move the ratchet body 3, the lever body 7*a* is upwardly rotated while resisting against the compression coil spring 4 and the ratchet body locking plate spring 6. Further, if the auxiliary compression coil spring 10 and the compression coil spring 11 for a leak preventive cover are provided, the lever body 7*a* is upwardly rotated while against these coil springs.

Further, the one end part of the pressing body 7*c* is axially supported at the backward side from the lever shaft 7*aa* of the lever body 7*a* of the lever 7. The pressing body 7*c* is constantly given the force for inserting the pressing pawl 7*ca* into the root part of the cogs of the rack part 3*cb* for ratchet of the ratchet body 3 at the frontward side from the locking pawl 6*a* of the ratchet body locking plate spring 6, where the pressing pawl 7*ca* is formed at the other end of the pressing body 7*c*. This force for inserting the pressing pawl 7*ca* is given by the spring 7*cb* for a pressing body provided between the pressing body 7*c* and the lever body 7*a*, as illustrated in FIGS. 3 to 6. The pressing body 7*c* supports a release body 8 using the pressing force given by the spring 7*cb* for a pressing body together with the ratchet body 3, where the release body 8 is provided between the both side wall parts 3*c*, 3*c* of the ratchet body 3. Further, when the portion at the backward side from the lever shaft 7*aa* of the lever body 7*a* is upwardly rotated, the pressing pawl 7*ca* frontwardly presses the root part of the cogs of the rack part 3*cb* for a ratchet of the ratchet body 3 so as to move the cogs the rack part 3*cb* for a ratchet to a just frontward position by one cog, as described above.

Further, the pressing body 7*c* constantly receives the force for being inserted into the root part of the cogs of the rack part 3*cb* for a ratchet of the ratchet body 3 by the spring 7*cb* for a pressing body. So, when the force for upwardly rotating the portion at the backward side from the lever shaft 7*aa* of the lever body 7*a* is canceled, the ratchet body 3 frontwardly moved is prevented to be moved in the front and rear directions by the ratchet body locking plate spring 6. Further, when the portion at the backward side from the lever shaft 7*aa* of the lever body 7*a* is returned to the initial position by the torsion spring 7*b*, the pressing pawl 7*ca* is pressed downwardly and gradually by the crest part of the cogs of the rack part 3*cb* for a ratchet while resisting against the spring 7*cb* for a pressing body, according to downwardly moving of the portion at the backward side from the lever shaft 7*aa* of the lever body 7*a*. Further, when the pressing pawl 7*ca* is downwardly rotated more so as to pass the top point of the cogs of the rack part 3*cb* for a ratchet, the pawl 7*ca* is inserted into a root part of the cogs just behind the above-described tooth by one cog, so as to be in the state that it can be moved again toward the front of the ratchet body 3.

Further, the spring 7*cb* for a pressing body of the pressing body 7*c* of the lever 7 is a compression coil spring provided between the pressing body 7*c* and the lever body 7*a*, which is not illustrated in the drawings, or a plate spring provided between the pressing body 7*c* and the lever body 7*a* as illustrated in FIGS. 3 to 6. Thereby, the spring 7*cb* for a pressing body can be suitably selected corresponding to the shapes of the housing body 5, the lever 7 and the like, so that it is preferable.

A release body 8 has a pressing part 8*a* provided between both sides wall parts 3*c*, 3*c* of the ratchet body 3, and a button part 8*b* which is continuously formed above the pressing part 8*a*, has a smaller area of a transverse section than that of a transverse section rectangular to the moving direction of the pressing part 8*a*, and is projected from the opening part 5*f* for a release body of the housing body 5. In the release body 8, when the button part 8*b* is downwardly pressed, the pressing part 8*a* downwardly moves the locking pawl 6*a* of the ratchet body locking plate spring 6 and the pressing pawl 7*ca* of the pressing body 7*c* of the lever 7, which are inserted into the root part of the cogs of the rack part 3*cb* for a ratchet of the ratchet body 3, so as to cancel the locking state with the rack part 3*cb* for a ratchet. The release body 8 is for backwardly moving the ratchet body 3 so as to return the piston rod 1 and the leak preventive cover 2 to the initial position.

The release body 8 is provided between the both side wall parts 3*c*, 3*c* of the ratchet body 3, in the state that the button part 8*b* is projected from the opening part 5*f* for a release body of the housing body 5, and in the state that the lower end of the pressing part 8*a* is positioned above the locking pawl 6*a* of the ratchet body locking plate spring 6 and the pressing pawl 7*ca* of the pressing body 7*c* of the lever 7. The locking pawl 6*a* and the pressing pawl 7*a* are inserted into the root part of the cogs of the rack part 3*cb* for a ratchet of the ratchet body 3, as illustrated in FIGS. 1 to 6. Further, when the button part 8*b* of the release body 8 is downwardly pressed, the pressing part 8*a* of the release body 8 is downwardly moved. According to backwardly moving of the pressing part 8*a*, the locking pawl 6*a* of the ratchet body locking plate spring 6 and the pressing pawl 7*ca* of the pressing body 7*c* of the lever 7, which are inserted into the root part of the cogs of the rack part for a ratchet 3*cb* of the ratchet body 3, are downwardly moved so as to cancel the locking state with the rack part 3*cb* for a ratchet. Therefore, the ratchet body 3 is backwardly pressed and returned to the initial position by the pressing force of the compression coil spring 4, which is compressed by contracting of the distance between the rear face of the leak preventive cover 2 and the front face of the frontward wall part 3*b* of the ratchet body 3. When the auxiliary compression coil spring 10 and the compression coil spring 11 for a leak preventive cover are provided, the ratchet body 3 is also pressed and returned to the initial position by these pressing forces.

Further, the reason that the button part 8*b* of the release body 8 is formed to have the smaller area of the transverse section than the area of transverse section rectangular to the moving direction of the pressing part 8*a* which is continuously formed below the button part 8*b* is as follows. If the area of the transverse section rectangular to the moving direction of the button part 8*b* is larger than the transverse section rectangular to the moving direction of the pressing part 8*a*, the pressing part 8*a* may enter into the opening part 5*f* for a release body of the housing body 5, or the pressing part 8*a* may be removed from the opening part 5*f* for a release body of the housing body 5, so that the release body 8 itself may be removed from the guiding path 5*c* of the housing body 5.

A stopper means 9 is for controlling to stop the ratchet body 3, which is backwardly moved by the pressing force of the compression coil spring 4, at the initial position when the locking state of the locking pawl 6*a* of the ratchet body locking plate spring 6 and the pressing pawl 7*ca* of the pressing body 7*c* of the lever 7 to the rack part 3*cb* for a ratchet is canceled by the release body 8. The stopper means 9 prevents run over of the piston rod 1, the leak preventive cover 2, ratchet body 3 and the compression coil spring 4 from the inside of the guiding path 5*c* of the housing body 5, when the ratchet body 3 is backwardly moved by the excess pressing force of the compression coil spring 4 so as to be moved behind initial position. Further, the stopper means 9 prevents removal of the small diameter portion 2*d* at the front end side of the leak preventive cover 2 from the supporting path 5*b* of the housing body 5.

As for the stopper means 9, for example, another projection for controlling to stop the ratchet body 3 at the initial position can be separately provided at the rear end of the guiding path 5*c* of the housing body 5, although the projection is not illustrated in the drawings. However, it is preferable, if a stopper means for controlling to stop the ratchet body 3 at the initial position can be formed by contacting the front end of a release body inserting part at the upward wall part 3*a* of the ratchet body 3, which is backwardly moved, to the button part 8*b* of the release body 8 and/or by contacting the rear end of the piston rod 1 fixed at the ratchet body 3, which is backwardly moved, to the pressing part 8*a* of the release body 8, as illustrated in FIGS. 3 to 6, because the stopper means can be made by only changing the shapes of the button part 8*b* of the release body 8 and the release body inserting part 3*aa* of the upward wall part 3*a* of the ratchet body 3, and the shape of the pressing part 8*a*.

Then, a method of using the pushing device of a tooth restoration material mixed and kneaded in a capsule according to the present invention having the above-described constitution is described.

When the ratchet body 3 is positioned at the front side from the initial position as illustrated in FIG. 4, that is, when the piston rod 1 and the leak preventive cover 2 are projected from the supporting path 5*b* of the housing body 5, an operation for returning the ratchet body 3 to the initial position is carried out as a preparation at first.

This operation is carried out by downwardly pressing the button part 8*b* of the release body 8. More particularly, when the button part 8*b* of the release body 8 is downwardly pressed, the locking pawl 6*a* of the ratchet body locking plate spring 6 and the pressing pawl 7*ca* of the pressing body 7*c* of the lever 7 are downwardly moved by the pressing part 8*a* of the release body 8, so as to cancel the locking state with the rack part 3*cb* for a ratchet, where these pawls are inserted into the root part of the cogs of the rack part 3*cb* for a ratchet of the ratchet body 3 before this operation. Further, the ratchet body 3 is backwardly pressed and moved to the initial position by the pressing force of the compression coil spring 4, which is compressed by contracting of the distance between the rear face of the leak preventive cover 2 and the front face of the frontward wall part 3*b* of the ratchet body 3 and the ratchet body 3 is also backwardly moved by the pressing forces of the auxiliary compression coil spring 10 and the compression coil spring 11 for a leak preventive cover when these are provided. Then, the backwardly moved ratchet body 3 is controlled so as to be stopped at the initial position by the stopper means 9.

Then, in the state that the ratchet body 3 is positioned at the initial position as illustrated in FIGS. 3 and 6, an operation for mounting the capsule C for a tooth restoration material on the mounting part 5*a* at the front end of the housing body 5 is carried out, where the powder component and the liquid component constituting a tooth restoration material such as a dental cement isolatedly housed in the capsule C in the predetermined amounts are mixed and kneaded by an automatic kneading device or the like.

For example, when the mounting part 5*a* of the housing body 5 has an engaging part which is formed projecting from the front end side of the supporting path 5*b* so as to engage to a groove part formed on the outer periphery of the rear end part of the capsule C for a tooth restoration material as illustrated in FIGS. 1 to 6, this operation is carried out by engaging the groove part of the rear end part of the capsule C for a tooth restoration material to the engaging part of the mounting part 5*a* as illustrated in FIG. 5.

After completing the above-described preparation, the front end opening part 2*a* of the leak preventive cover 2 is contacted to the rear end part of the capsule C for a tooth restoration material mounted on the mounting part 5*a* of the housing body 5. This operation is carried out by upwardly rotating a portion at the backward side from the lever body 7*a* of the lever 7, while resisting against the rotating force given by the torsion spring 7*b*, and against the pressing forces by the compression coil spring 4 and the ratchet body locking plate spring 6, and also against the forces by the auxiliary compression soil spring 10 and the compression coil spring 11 for a leak preventive cover when these are provided, similarly to the ordinary lever operation for pushing out the tooth restoration material housed in the capsule C for a tooth restoration material.

At this time, when the portion at the backward side from the lever body 7a of the lever 7 is upwardly rotated, the pressing pawl 7ca formed at another end of the pressing body 7c frontwardly presses the root part of the cogs of the rack part 3cb for a ratchet of the ratchet body 3 so as to move the cogs of the rack part 3cb for a ratchet to the just frontward position by one cog, where one end part of the pressing body 7c is axially supported at the backward side from the lever shaft 7aa of the lever body 7a and the pressing pawl 7ca is formed at another end thereof. However, the leak preventive cover 2, which is inserted with the piston rod 1 in the state of not frontwardly moving more by the head part 1a of the piston rod 1 fixed at the ratchet body 3, as illustrated in FIGS. 7 and 8, is in the state of being pressed constantly and frontwardly by the compression coil spring 4, which is provided along the outer periphery of the piston rod 1, between the rear face of the leak preventive cover 2 and the front face of the frontward wall part 3b of the ratchet body 3. The leak preventive cover 2 is also in the state that the inner face of the housing part 2b thereof is contacted with the head part 1a of the piston rod 1. Therefore, when the ratchet body 3 is frontwardly moved in these states, the leak preventive cover 2 frontwardly slides in the supporting path 5b of the housing body 5 in the state that the inner face of the housing part 2b of the cover 2 is contacted with the head part 1a of the piston rod 1, as illustrated in FIG. 4, and finally, the front end opening part 2a of the cover 2 is contacted with the rear end part of the capsule C for a tooth restoration material.

Further, in the case that the compression coil spring 11 for a leak preventive cover having smaller spring constant than that of the compression coil spring 4 is provided along the outer periphery of the leak preventive cover 2 between the flange part 2f formed on the rear end outer periphery of the leak preventive cover 2, and the front end in the guiding path 5c of the housing body 5 as illustrated in FIGS. 3 to 5, when the portion at the backward side from the lever body 7a of the lever 7 is upwardly rotated so as to frontwardly move the ratchet body 3, the distance between the front end in the guiding path 5c of the housing body 5 and the front face of the frontward wall part 3b of the ratchet body 3 contracts, so that the pressing forces by the compression coil spring 4 and the compression coil spring 11 for a leak preventive cover are increased. However, since the spring constant of the compression coil spring 11 for a leak preventive cover is smaller than that of the compression coil spring 4, the compression coil spring 11 for a leak preventive cover is compressed first as it is beaten by the pressing force by the compression coil spring 4. Thus, after the distance between the flange part 2f and the front end in the guiding path 5c of the housing body 5 contracts first, the distance between the rear face of the leak preventive cover 2 and the front face of the frontward wall part 3b of the ratchet body 3 contracts. Therefore, the leak preventive cover 2 frontwardly slides in the supporting path 5b of the housing body 5, and finally, the front end opening part 2a of the cover 2 contacts to the rear end part of the capsule C for a tooth restoration material.

Then, an operation for pushing out a tooth restoration material housed in the capsule C for a tooth restoration material is carried out by upwardly rotating the portion at the backward side from the lever body 7a of the lever 7 repeatedly so as to frontwardly move the piston rod 1.

The operation for upwardly rotating the portion at the backward side from the lever body 7a of the lever 7 is carried out at first while resisting against the rotating force given by the torsion spring 7b and the pressing forces by the compression coil spring 4 and the ratchet body locking plate spring 6, and also against the forces by the auxiliary compression coil spring 10 and the compression coil spring 11 for a leak preventive cover if these springs are provided, similarly to the operation for contacting the front end opening part 2a of the leak preventive cover 2 with the rear end part of the capsule C for a tooth restoration material mounted on the mounting part 5a of the housing body 5. Thereby, the pressing pawl 7ca formed at another end of the pressing body 7c, one end part of which is axially supported at the backward side from the lever shaft 7aa of the lever body 7a, frontwardly presses the root part of the cogs of the rack part 3cb for a ratchet of the ratchet body 3 so as to frontwardly move the cogs of the rack part 3cb for a ratchet to the just frontward position by one cog. Then, the piston rod 1 fixed at the ratchet body 3 also moves the cogs of the rack part 3cb for a ratchet to the just frontward position by one cog.

In this case, the locking pawl 6a of the ratchet body locking plate spring 6, which is inserted into a root part of the cogs positioned at the backward side from the root part of the cogs of the rack part 3cb for a ratchet of the ratchet body 3 inserted with the pressing pawl 7ca, is pressed gradually and downwardly by the crest part of the cogs of the rack part 3cb for a ratchet according to frontwardly moving of the rack part 3cb for a ratchet, and thereby, the rack part 3cb for a ratchet is frontwardly moved more. Then, when the locking pawl 6a passes the top point of the cogs of the rack part 3cb for a ratchet, the locking pawl 6a is inserted into the root part of the cogs which is just behind the above-described cogs, so as to be again in the state of preventing move of the ratchet body 3 in the front and rear directions. So, the piston rod 1 fixed at the ratchet body 3 also keep the state that the cogs of the rack part 3cb for a ratchet is moved to the just frontward position by one cog.

Then, when the force for upwardly rotating the portion at the backward side from the lever shaft 7aa of the lever body 7a of the lever 7 is canceled from the above-described state, since the ratchet body 3 is prevented to be moved in the front and rear directions by the locking pawl 6a of the ratchet body locking plate spring 6 inserted into the root part of the cogs of the rack part 3cb for a ratchet of the ratchet body 3, the pressing pawl 7ca of the pressing body 7c, which is constantly given the force for being inserted into the root part of the cogs of the rack part 3cb for a ratchet of the ratchet body 3 by the spring 7cb for a pressing body, is downwardly and gradually pressed by the crest part of the cogs of the rack part 3cb for a ratchet while resisting against the spring 7cb for a pressing body according to downwardly rotating of the lever body 7a when it returns to the initial position by torsion spring 7b. Further, when the pressing pawl 7ca is downwardly rotated more so as to pass the top point of the cogs of the rack part 3cb for a ratchet, the pressing pawl 7ca is inserted into a root part of the cogs which is just behind the above-described cogs by one cog, so as to be in the state that it can be moved again toward the front of the ratchet body 3 by one cog.

Then, the operation for upwardly rotating the portion at the backward side from the lever body 7a of the lever 7, and the operation for canceling the force for upwardly rotating the portion at the backward side from the lever body 7a of the lever 7 are repeated, so as to frontwardly and successively move the piston rod 1 fixed at the ratchet body 3, and thereby, the tooth restoration material housed in the capsule C for a tooth restoration material can be pushed out as illustrated in FIG. 5.

In this case, even if the residual powder component or the like which is not mixed and kneaded in the capsule body of the capsule C for a tooth restoration material is jetted from the rear end part of the capsule C for a tooth restoration material by pressing the capsule C, the front end opening part 2a of the leak preventive cover 2 is already contacted with the rear end part of the capsule C for a tooth restoration material as illustrated in FIG. 5. So, the jetted powder component or the like is not jetted to the outside due to the existence of the leak preventive cover 2, but enters into the housing body 5 through the through hole 1b of the piston rod 1 from the slit 1c and the opening of the through hole 1b of the piston rod 1. Therefore, it can be prevented that the powder component or the like is poured on a face of a patient or a dentist, and a patient or a dentist inhales it by mistake.

Finally, after pushing out a desired amount of the tooth restoration material from the capsule C for a tooth restoration material, when the used capsule C for a tooth restoration material mounted on the mounting part 5a of the housing body 5 is returned to be detachable state, an operation for backwardly moving the ratchet body 3 by downwardly pressing the release body 8 so as to return the piston rod 1 and the leak preventive cover 2 to the initial position is carried out. As a result of this operation, the front end part of the piston rod 1 inserted into the capsule body of the capsule C for a tooth restoration material can be removed from the inside of the capsule body of the capsule C for a tooth restoration material.

In this operation, when the button part 8b of the release body 8 is downwardly pressed, the pressing part 8a continuously formed with the button part 8b is downwardly moved, and thereby, the locking pawl 6a of the ratchet body locking plate spring 6 and the pressing pawl 7ca of the pressing body 7c of the lever 7, which are inserted into the root part of the cogs of the rack part 3cb for a ratchet of the ratchet body 3, are downwardly moved, so as to cancel the locking state with the rack part 3cb for a ratchet. So, the ratchet body 3 is backwardly pressed and moved to the initial position by the pressing force by the compression coil spring 4, which is compressed by contracting of the distance between the rear face of the leak preventive cover 2 and the front face of the frontward wall part 3b of the ratchet body 3, and also by the pressing forces by the auxiliary compression coil spring 10 and the compression coil spring 11 for a leak preventive cover if these springs are provided. Further, the backwardly moved ratchet body 3 is controlled to be stopped at the initial position by the stopper means 9.

After the ratchet body 3 is backwardly moved by downwardly pressing the release body 8 so as to return the piston rod 1 and the leak preventive cover 2 to the initial position, the used capsule C for a tooth restoration material mounted on the mounting part 5a of the housing body 5 can be removed.

What is claimed is:

1. A pushing device for a tooth restoration material mixed and kneaded in a capsule, comprising:
    a cylindrical piston rod for pushing a tooth restoration material housed in a capsule for a tooth restoration material, the piston rod having a head part and a through hole, where the head part has at least a part, which has a larger outer diameter than an outer diameter of the backward side, at the front end side, and the through hole is provided along the whole length of the piston rod, and having at least more than one slit at a front end thereof and locking through holes provided in a side part at the rear end side thereof, where the locking through holes have a smaller diameter than that of the through hole, reach to the through hole, and are opposed each other;
    a leak preventive cover having a front end opening part contacted with a rear end part of the capsule for a tooth restoration material to be mounted, a housing part for housing the head part of the piston rod, an inserting hole for inserting a portion at the backward side from the head part of the piston rod slidably in the axial direction at the backward side of the housing part, and a small diameter portion and a large diameter portion on the outer periphery thereof, where the small diameter portion is provided at the front end side, and the large diameter portion is provided at the rear end side;
    a ratchet body having an upward wall part having a release body inserting part from the frontward side to the backward side at a center part in the width direction, a frontward wall part having a piston rod inserting hole provided for inserting the rear end part of the piston rod, and both side wall parts having a hole for a piston rod fixing pin provided through at the frontward side, and having a rack part for a ratchet formed on a lower edge at the rear side of the hole for a piston rod fixing pin, where the piston rod inserted into the piston rod inserting hole is fixed by a piston rod fixing pin, which is inserted into the both locking through holes of the piston rod, and the both holes for a piston rod fixing pin;
    a compression coil spring provided along the outer periphery of the piston rod, between a rear face of the leak preventive cover and a front face of the frontward wall part of the ratchet body;
    a housing body having a mounting part at which the capsule for a tooth restoration material is mounted, a supporting path for slidably inserting the small diameter portion of the leak preventive cover, a guiding path in which the piston rod, the compression coil spring and the ratchet body are provided movably in front and rear directions while contacting to the upward wall part of the ratchet body, a through hole for a lever shaft provided at the both side wall parts at a lower side of the guiding path, a grip part provided at the rear end side of the guiding path, and an opening part for a release body at a position of an upper side of the guiding path, where the position of the opening part for the release body is at least connected to the release body inserting part of the ratchet body when the ratchet body is moved at the most backward side so as to be positioned at an initial position and where the mounting part, the supporting path and the guiding path are provided in this order from a front end toward the back at an upper part of the housing body;
    a ratchet body locking plate spring, which is for constantly giving force for upwardly pressing the ratchet body so as to prevent movement of the ratchet body in the front and rear directions, and the rear end of the plate spring is fixed at the backward side from the guiding path in the housing body a locking pawl which is at the front of the plate spring is inserted into a root part of the cogs of the rack part for a ratchet of ratchet body;
    a lever having a lever body rotatably mounted on a lever shaft fixed at the through hole for a lever shaft of the housing body, a torsion spring being provided along the outer periphery of the lever shaft and constantly giving force for downwardly rotating the backward side from the lever shaft of the lever body, and a pressing body having one end part axially supported at the backward side from the lever shaft of the lever body and constantly receiving a force for inserting a pressing pawl formed at another end thereof into the root part of the cogs of the rack part for a ratchet of the ratchet body which is positioned at the frontward side from the locking pawl of the ratchet body locking plate spring, where the force is given by a spring for a pressing body provided between the pressing body and the lever body, and where, when a portion at the backward side from the lever shaft of the lever body is upwardly rotated while resisting against the rotating force given by the torsion spring and the pressing forces given by the compression coil spring and the ratchet body locking plate spring, the pressing pawl of the pressing body frontwardly presses the root part of the cogs of the rack part for a ratchet of the ratchet body so as to frontwardly move the cogs of the rack part for a ratchet body by just one cog, and when the force for upwardly rotating the portion at the backward side from the lever shaft of the lever body is canceled, the pressing pawl of the pressing body is inserted into a root part of the cogs, which is just one cog behind the cogs of the rack part for a ratchet moved by the pressing pawl of the pressing body, so as to return the lever body to the initial position;

The release body having a pressing part provided between the both side wall parts of the ratchet body, and a button part which is continuously formed above the pressing part, has a smaller area of a transverse section than an area of a transverse section rectangular to the moving direction of the pressing part, and is projected from the opening part for a release body of the housing body, where, when the button part is downwardly pressed, the pressing part downwardly moves the locking pawl of the ratchet body locking plate spring and the pressing pawl of the pressing body of the lever, which are inserted into the root part of the cogs of the rack part for a ratchet of the ratchet body, so as to cancel the locking state to the rack part for a ratchet; and a stopper means for controlling to stop the ratchet body, which is backwardly moved by the pressing force of the compression coil spring, at the initial position, when the locking state of the locking pawl of the ratchet body locking plate spring and the pressing pawl of the pressing body of the lever to the rack part for a ratchet is canceled by the release body; wherein an auxiliary compression coil spring is provided along the outer peripheries of the leak preventive cover and the compression coil spring, between a front end side of the guiding path of the housing body and the frontward wall part of the ratchet body.

2. The pushing device for a tooth restoration material mixed and kneaded in a capsule as claimed in claim 1 wherein a compression coil spring for the leak preventive cover having a smaller spring constant than that of the compression coil spring is provided along the outer periphery of the leak preventive cover, between a flange part formed on a rear end outer periphery of the leak preventive cover and the front end of the guiding path of the housing body.

3. The pushing device for a tooth restoration material mixed and kneaded in a capsule as claimed in claim 1, wherein the housing part of the leak preventive cover has a shape having a diameter which is made gradually larger toward the front end thereof.

4. The pushing device for a tooth restoration material mixed and kneaded in a capsule as claimed in claim 1, wherein the spring for a pressing body of the pressing body of the lever is a compression coil spring provided between the pressing body and the lever body.

5. The pushing device for a tooth restoration material mixed and kneaded in a capsule as claimed in claim 1, wherein the spring for a pressing body of the pressing body of the lever is a plate spring provided between the pressing body and the lever body.

6. The pushing device for a tooth restoration material mixed and kneaded in a capsule as claimed in claim 1, wherein the stopper means controls to stop the ratchet body at the initial position by contacting a front end of the release body inserting part of the upward wall part of the backwardly moved ratchet body to the button part of the release body, and by contacting a rear end of the piston rod fixed at the backwardly moved ratchet body to the pressing part of the release body.

7. The pushing device for a tooth restoration material mixed and kneaded in a capsule as claimed in claim 1, wherein a smooth sliding member made of a synthetic resin and contacted with an inner face of the guiding path of the housing body is adhered on an upper face of the upward wall part and side faces of the both side wall parts of the ratchet body.

* * * * *